United States Patent [19]

Dormia

[11] 4,347,846

[45] Sep. 7, 1982

[54] SURGICAL EXTRACTOR

[75] Inventor: Enrico Dormia, Lecco, Italy

[73] Assignee: Porges, Paris, France

[21] Appl. No.: 196,866

[22] Filed: Oct. 14, 1980

[30] Foreign Application Priority Data

Dec. 7, 1979 [IT] Italy .................................. 27940 A/79

[51] Int. Cl.³ ............................................. A61B 17/00
[52] U.S. Cl. .................................................... 128/328
[58] Field of Search .......................... 128/328, 345, 356

[56] References Cited

U.S. PATENT DOCUMENTS 4,046,150 9/1977 Schwartz et al. ..................... 128/328
4,198,960 4/1980 Utsugi .............................. 128/328 X

FOREIGN PATENT DOCUMENTS 2821048 11/1979 Fed. Rep. of Germany ...... 128/328
597537 8/1959 Italy .................................... 128/328

*Primary Examiner*—Michael H. Thaler
*Attorney, Agent, or Firm*—Merriam, Marshall & Bicknell

[57] ABSTRACT

The present invention relates to a surgical extractor for removing foreign bodies from natural passages, of the type constituted by a flexible tube adapted to penetrate in the natural passages where the body to be extracted is located, the distal end of the tube comprising a cage or basket formed by steel wires which are retractable inside the tube in the positioning phase and adapted to be opened out for imprisoning the body to be extracted, expansion being ensured by maneuvering a steel wire housed in said tube and adapted to be maneuvered from the outside, wherein the retractable cage is formed by a plurality of flexible metal wires, for example steel wires, disposed in a helical path, certain of the wires following a helix in clockwise direction, while other wires, in equal number, follow a helix in anti-clockwise direction.

2 Claims, 5 Drawing Figures

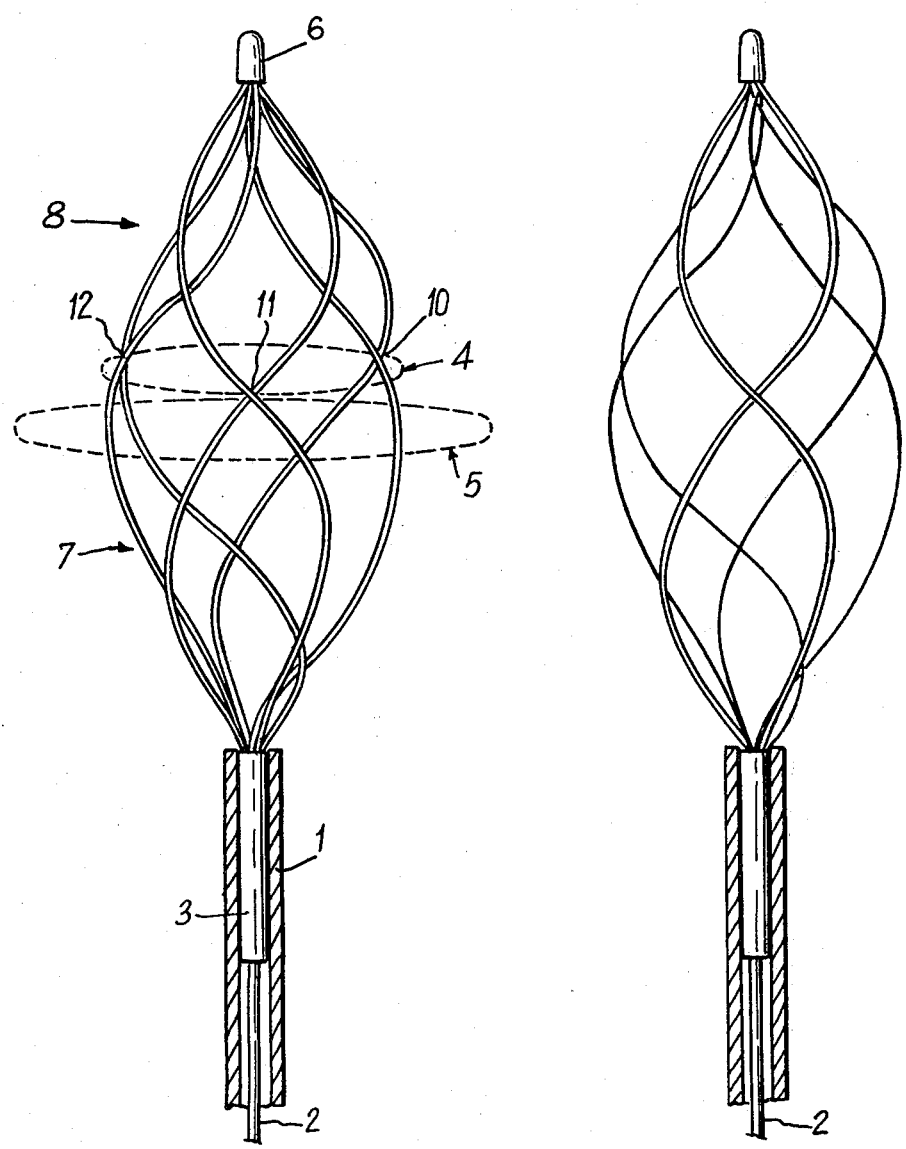

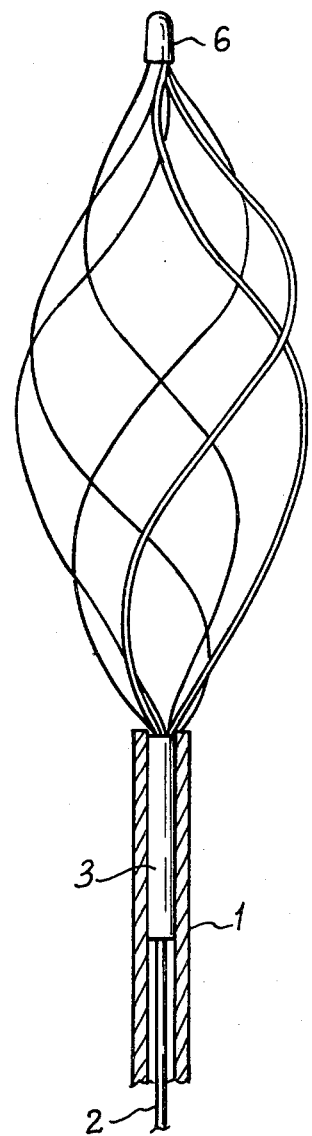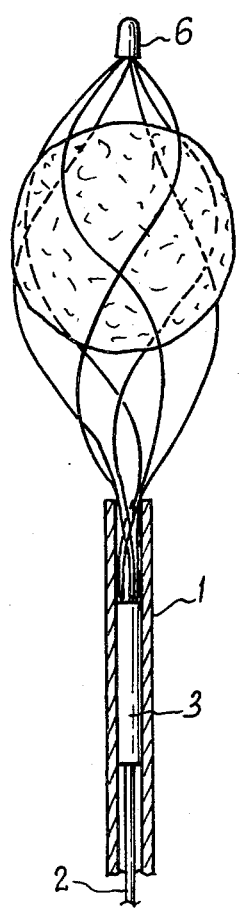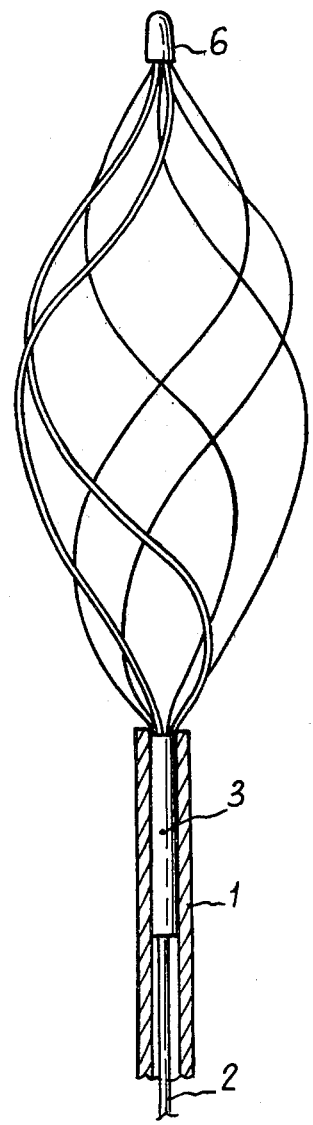

SURGICAL EXTRACTOR

The present invention relates to a device for extracting foreign bodies found in natural passages in the body, such as in the urinary tract, bile duct, blood vessels...

Devices are known which are used in particular in urology, for example for extracting a calculus from the ureter.

French Patent No. 1 197 808 in particular describes an instrument for making an extraction of this type; this instrument is constituted by a flexible tubular guide adapted to penetrate along the natural passages up to the spot where the body to be extracted is located; the tube contains a wire, for example made of steel, for controlling the manoeuvre, at the distal end of the tube, of a basket-like element formed by flexible wires, for example by an assembly of steel wires; this basket may retract inside the tube (for penetration of the latter in the natural passages) and it may open out, due to the manoeuvre of the steel wire, to imprison the body, for example the calculus; retraction of the basket will ensure total imprisonment of the calculus and retraction of the tube will enable the whole to be removed with the calculus imprisoned in the basket.

Various forms of basket or cage are known for ensuring greater efficiency, i.e. ensuring on the one hand manoeuvre of the basket when it passes from the retracted position to expanded position by opening out the wires constituting the bars of the cage adapted to imprison the body, then holding of the latter when the instrument is being withdrawn.

It will be seen that the cage or basket shapes must ensure a trap effect, i.e. facilitated passage of the body, for example a calculus or clot, inside the cage but then prevent escape thereof when it is in place in the cage and evacuated with the withdrawal of the instrument.

The shapes of wires forming the bars of the basket or cage as heretofore known, do not satisfy this double imperative.

In fact, in the shapes given to the wire constituting the bars of this retractable cage, the wires, in expanded position, follow parallel paths.

When these wires follow a helical path, a generally more enveloping shape is obtained; however, due to the spacing of the bars, small-sized bodies in particular escape between two adjacent bars, during the retraction manoeuvre.

It is an object of the present invention to remedy this drawback by providing an extractor of which the cage has the double advantage of facilitating penetration of the body during the imprisonment phase, whilst holding and blocking the body when the latter is held and present in the cage.

To this end, the invention relates to a surgical extractor for removing foreign bodies along the natural passages, of the type constituted by a flexible tube adapted to penetrate into the natural passages where the body to be extracted is located, the distal end of the tube comprising a cage composed of steel wires which are retractable inside the tube in the positioning phase and capable of being opened out to imprison the body to be extracted, the expansion being ensured by manoeuvring a steel wire housed in said tube and adapted to be manoeuvred from the outside, the extractor being characterised in that the retractable cage is formed by a plurality of flexible metal wires, for example steel wires, disposed in a helical path, whilst other wires, in equal number, follow a helix in anticlockwise direction.

A cage is thus produced whose wires intersect in pairs.

The points of intersections constitute zones where the body will be definitely imprisoned, being held firmly, without risk of escape between two parallel wires (as in the prior known extractors).

According to a prefered embodiment of the invention, the point of intersection of the two wires, clockwise and anti-clockwise respectively, is located beyond the equatorial plane of the cage (in the form of a spindle).

According to this feature, it will be understood that as the zones to intersection are located towards the distal end of the cage, the latter is of dissymmetrical structure.

The low part of the cage (located near the tube) comprises wires which are spaced apart without intersecting; it is precisely through this zone that the body penetrates inside the cage.

In fact, it is known that, when using an extractor of this type, the end of the tube is brought in the immediate vicinity of the calculus or body to be extracted; and the cage opens out beyond the calculus or body so that the latter is substantially at the level of the lower part of the cage where there is no intersection of wires and where, consequently, the wires forming bars are adapted to the penetration of the body and can easily envelop it.

On the contrary, in the upper or terminal part of the cage are found the zones of intersection of two wires, this zone forming a barrier, due to the intersection of the wires, imprisoning the body.

The extraction manoeuvre begins by a contracting of the cage, which is partially retracted inside the tube, so that the low part of the cage (or "open" part) will be retracted inside the tube and placed in inactive position; the calculus or body to be extracted is then held in the upper part of the cage which precisely constitutes the "closed" part due to the wire intersections.

Under these conditions, it will be understood that the body may penetrate in an extractor according to the invention as easily as in a conventional extractor, but, once in the cage, the latter prevents any accidental escape.

The present invention therefore improves efficiency in the extraction manoeuvre and has proved particularly effective, during the tests and experiments which have been carried out, in difficult cases such as sand in the ureter, microlithiasis in the bile duct, and obstruction of the blood vessels.

In addition, the arrangement of the wires under the conditions described hereinabove avoids during extraction, any danger of twisting of the passage in which the extractor is inserted, contrary to what may occur with the cage composed of parallel wires.

By using the arrangement provided in the present invention, wires of vary small dimensions, of up to 2/10th millimeter, may be used.

During the manoeuvre for retracting the extractor, a greater stability of the whole is therefore obtained, which allows th doctor to work under more reliable and more efficient conditions than before.

The invention will be more readily understood on reading the following description with reference to the accompanying drawings, in which:

FIG. 1 shows a view in perspective of a cage disposed at the end of an extractor according to the invention.

FIGS. 2, 3 and 4 successively show, to clarify the invention, the three pairs of wires (each formed by a clockwise helical wire and by an anti-clockwise helical wire) constituting the extractor according to the invention.

FIG. 5 shows a view of the extractor according to FIG. 1, after imprisonment of a calculus and after partial retraction of the cage.

Referring not to the drawings, the extractor is composed in conventional manner of a flexible tube 1 in which penetrates the manoeuvring wire, for example the steel wire 2 which acts on the terminal cylinder 3 sliding at the end of the tube 1.

The wires which form the extraction cage according to the invention emerge from the cylinder 3.

It will be seen that, depending on the manoeuvre of the sliding cylinder 3, controlled by the wire 2, the wires of the cage may retract inside the end of the tube 1 and subsequently open out, inside the passage where the calculus is located, to imprison the latter.

In the example described here, the cage is composed of six wires, viz, three wires disposed helically in clockwise direction, and three other wires disposed helically in anti-closkwise direction.

To clarify the drawings, FIGS. 2, 3 and 4 each successively show pairs of wires, each pair comprising a clockwise wire and an anti-clockwise wire.

These wires (belonging to the same pair) intersect at a level represented by circle 4 (FIG. 1).

According to a feature of the invention, the transverse plane 4 corresponding to the level of the intersections of the wires is located above and towards the distal end 6 with respect to the plane 5 which corresponds to the equatorial plane of the spindle formed by the cage.

It is thus seen that, in the lower zone 7, the wires do not intersect and, under these conditions, they form an open structure allowing the calculus to penetrate easily.

On the contrary, in the upper part 8, the zones of intersection 4 form a closed structure which enables the calculus to be firmly imprisoned.

FIG. 5 shows the phase of imprisonment of the calculus; the lower part of the cage is partially closed by penetration in the tube and the calculus is thus forced back towards the upperpart of the cage, i.e. the closed part where the intersections 10,11 and 11' of the wires (FIG. 1) will imprison the calculus firmly.

What is claimed is:

1. In a surgical extractor for removing bodies from natural passages, of the type comprising a flexible tube adapted to be inserted in a natural passage where the body to be extracted is located, the distal end of the tube having a retractable cage formed by flexible metal wires which are retractable inside the tube for positioning the tube in the passage and extendable for trapping the body to be extracted, the improvement wherein the retractable cage is formed by a plurality of flexible metal wires arranged in pairs and disposed in helical paths, one wire of each pair being spiralled in clockwise direction and the other in anti-clockwise direction, the wires of each pair intersecting at a single point between the ends thereof, the spacing between wires in said cage being sufficient to permit the passage of said body into the interior of said cage.

2. An extractor in accordance with claim 1 wherein said point of intersection lies substantially in a plane located between the equitorial plane of the cage and the distal end thereof, whereby the cage comprises a relatively open proximal face in which the wires are relatively widely spaced, allowing free passage for the body to be trapped, and a relatively closed distal face in which the intersecting wires impede passage therethrough of the trapped body.

* * * * *

UNITED STATES PATENT AND TRADEMARK OFFICE
CERTIFICATE OF CORRECTION

PATENT NO. : 4,347,846
DATED : September 7, 1982
INVENTOR(S) : ENRICO DORMIA

It is certified that error appears in the above-identified patent and that said Letters Patent are hereby corrected as shown below:

Col. 1, line 35, "facilitated" should be --facilitate--.

Col. 2, line 1, after "path", insert the following

--certain of the wires following a helix in clockwise direction--.

Signed and Sealed this

Fifteenth Day of February 1983

[SEAL]

Attest:

Attesting Officer

GERALD J. MOSSINGHOFF
Commissioner of Patents and Trademarks